United States Patent [19]

Safir et al.

[11] 4,066,647

[45] Jan. 3, 1978

[54] SUBSTITUTED 6-(PIPERAZINYL)-10H-PYRIDO[3,2-B]THIENO[3,4-E][1,4]-DIAZEPINES

[75] Inventors: Sidney Robert Safir, River Edge; Corris Mabelle Hofmann, Ho-Ho-Kus, both of N.J.

[73] Assignee: American Cyanamid Company, Stamford, Conn.

[21] Appl. No.: 741,423

[22] Filed: Nov. 12, 1976

[51] Int. Cl.$^2$ ............................................ C07D 495/14
[52] U.S. Cl. ............................... 260/268 TR; 424/250
[58] Field of Search .................. 260/268 TR; 424/250

[56] References Cited

U.S. PATENT DOCUMENTS

| 3,951,981 | 4/1976 | Safir | 260/268 TR |
| 3,953,430 | 4/1976 | Safir | 260/239.3 T |

Primary Examiner—Paul M. Coughlan, Jr.
Assistant Examiner—Jose Tovar
Attorney, Agent, or Firm—Norton S. Johnson

[57] ABSTRACT

Various substituted 6-(piperazinyl)10H-pyrido[3,2-b]thieno[3,4-e][1,4]-diazepines which have demonstrated anti-psychotic activity are disclosed.

1 Claim, No Drawings

SUBSTITUTED 6-(PIPERAZINYL)-10H-PYRIDO[3,2-b]THIENO[3,4-e][1,4]-DIAZEPINES

Description of the Prior Art

U.S. Pat. No. 3,953,430, Safir, discloses lactams of the following formula:

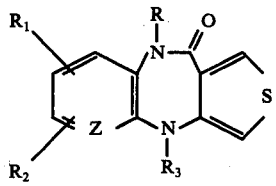

More specifically, the compounds where Z is N and R, and $R_1$ and $R_2$ are H are the starting materials for the preparation of the compounds of the present invention.

SUMMARY OF THE INVENTION

This application discloses novel compounds of the formula:

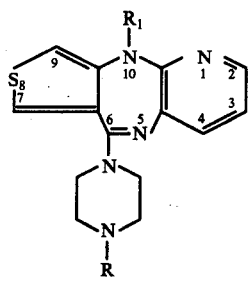

wherein R is selected from the group consisting of hydrogen, lower alkyl and hydroxy lower alkyl; $R_1$ is selected from the group consisting of hydrogen and lower alkyl, and pharmaceutically acceptable acid addition salts thereof.

This application is concerned also with methods and compositions of matter thereof for the therapeutic management of the manifestations of psychotic disorders, psychoneurotic conditions, anxiety and tension in warm-blooded animals by administering compounds of the claimed invention.

The compounds of the present invention may be prepared by the following sequence:

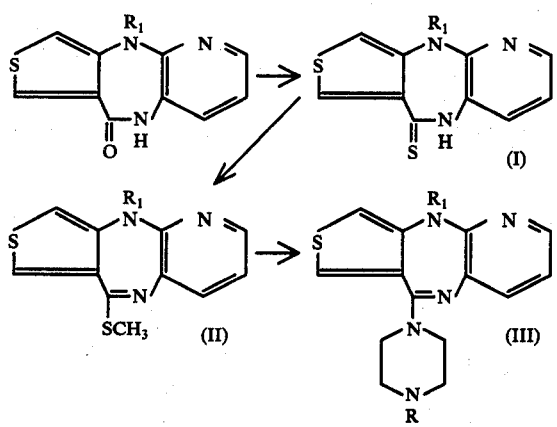

wherein R and $R_1$ are as defined above.

The starting material, a substituted 5,10-dihydro-6H-pyrido[3,2-b]thieno[3,4-e][1,4]diazepin-6-thione (I), is prepared from the reaction of the corresponding 5,10-dihydro-6H-pyrido[3,2-b]thieno[3,4-e][1,4]diazepin-6-one (described in U.S. Pat. No. 3,953,430) and phosphorus pentasulfide in a solvent such as pyridine at reflux. This intermediate (I) is then converted to the correspondingly substituted 6-(methylthio)-10H-pyrido[3,2-b]thieno[3,4-e][1,4]diazepine (II) by reaction with a strong base such as sodium methoxide or sodium hydride and methyl iodide or methyl sulfate in a suitable solvent such as ethanol or dimethylformamide. The latter reaction is carried out at from 25° C to 45° C for a period of from about ½ to 3 hours. The intermediate (II) is converted to the corresponding 6-substituted piperazinyl-10H-pyrido[3,2-b]thieno[3,4-e][1,4]diazepine by reaction with the appropriate piperazine at reflux temperature either neat or in a solvent such as xylene containing a catalystic amount of acetic acid. The reaction is heated from 3 to 24 hours at a temperature which may vary from 100° C to 175° C.

Specific compounds included within the scope of this invention are:
6-(4-Methyl-1-piperazinyl)-10H-pyrido[3,2-b]thieno[3,4-e][1,4]-diazepine,
6-(1-Piperazinyl)-10H-pyrido[3,2-b]thieno[3,4-e][1,4]diazepine, fumarate,
4-(10H-Pyrido[3,2-b]thieno[3,4-e][1,4]diazepin-6-yl)-1-piperazineethanol, fumarate,
10-Methyl-6-(4-methyl-1-piperazinyl)-10H-pyrido[3,2-b]thieno-[3,4-e][1,4]diazepine.

DESCRIPTION OF THE PREFERRED EMBODIMENTS

The compounds of the present invention are physiologically active on the central nervous system and show high activity as anti-psychotic or neuroleptic agents. A useful test for anti-psychotic activity consists of measuring the reduction of spontaneous motor activity in animals.

Groups of 4 rats are treated orally with the test compound dissolved or suspended in starch vehicle at the maximum tolerated dose. At the estimated time of peak effect, the animals are placed singly into an Animex Activity Counter ® and the activity of each rat is recorded over a 5 minute period. The activity counts are compared to historical or parallel control values to determine significant decreased locomotor activity. The compound is considered an active depressant if the counts are 50% or less of control values.

Median effective doses ($MDD_{50}$) (doses which decrease locomotor activity by 50%) are determined, in groups of 6 rats, for those compounds deemed active, by a method of least-squares [D. F. Finney, Statistical Methods in Biological Assay, Second Edition, Hofner Publishing Co., New York, 456-457 (1964)]. The effective dose that causes a 50% reduction in motor activity ($MDD_{50}$) of a typical compound, for example, 6-(4-methyl-1-piperazinyl)-10H-pyrido[3,2-b]thieno(3,4-e][1,4]-diazepine is 9 mg/kg of body weight.

The active components of this invention can be used in compositions such as tablets; the principal active ingredient is mixed with conventional tableting ingredients, such as corn starch, lactose, sucrose, sorbitol, talc, stearic acid, magnesium stearate, dicalcium phosphate, gums or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating.

The liquid forms in which the novel compositions of the present invention may be incorporated for administration include suitably flavored emulsions with edible oils, such as cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for a warm-blooded animal subject, each unit containing a predetermined quantity of active component calculated to produce the desired therapeutic effect in association with the required pharmaceutical diluent carrier or vehicle. The dosage may vary from one to 70 mg/kg of warm-blooded animal per day, preferably in multiple doses. The daily dosage requirement may be from 50 to 2000 mg. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

EXAMPLE 1

6-(4-Methyl-1-piperazinyl)-10H-pyrido[3,2-b]thieno-[3,4-e][1,4]diazepine

A mixture of 27.1 g of 5,10-dihydro-6H-pyrido[3,2-b]thieno[3,4-e][1,4-diazepin-6-one (prepared according to the general method described in U.S. Pat. No. 3,953,430) and 11.1 g of phosphorus pentasulfide in 250 ml of dry pyridine is stirred and heated under reflux for 4 hours. Excess pyridine is removed and 300 ml of 5% aqueous sodium carbonate and some methanol is added to the residue followed by overnight stirring. The pH of the resulting mixture is adjusted to 7.0 with dilute hydrochloric acid. The brown solid is collected and washed with water to give 25.7 g of 5,10-dihydro-6H-pyrido-[3,2-b]thieno[3,4-e][1,4]diazepin-6-thione, mp 255°–260° C.

A 2.3 g portion of sodium metal is dissolved in 400 ml of ethyl alcohol with stirring then 23.3 g of the above compound and 15 ml of methyl iodide is added and stirring is continued overnight. The resulting mixture is cooled and filtered with collection of a brown solid. The solid is extracted with ether in a Soxhlet-thimble, the ether is evaporated and the yellow solid is recrystallized from methyl alcohol to give 6-(methylthio)-10H-pyrido[3,2-b]thieno[3,4-e]-[1,4]diazepine, mp 138°–140° C.

A 2.5 g portion of the above compound, 16.0 ml of N-methylpiperazine and 3 drops of glacial acetic acid is stirred at reflux temperature (138° C) for 7 ½ hours then is poured into ice-water. The yellow solid formed is collected and recrystallized from ethanol to give the product of the example, mp 189°–191° C.

EXAMPLE 2

6-(1-Piperazinyl)-10H-pyrido[3,2-b]thieno[3,4-e][1,4]-diazepine, fumarate

A mixture of 2.5 g of 6-(methylthio)-10H-pyrido-[3,2-b]thieno[3,4-e][1,4]diazepine (prepared as described in Example 1), 8.6 g of piperazine, 15 ml of xylene and 3 drops of glacial acetic acid is stirred at reflux temperature (135°–140° C) overnight. The solvent is evaporated and the residue is washed with water and is dissolved in 50 ml of dilute acetic acid. The solution is filtered, the filtrate is made alkaline with ammonium hydroxide and is extracted several times with methylene chloride. The extracts are dried over magnesium sulfate, then filtered and evaporated to dryness. The residue is dissolved in 30 ml of methyl alcohol and treated with a solution of 2.3 g of fumaric acid in 45 ml of ethyl alcohol. The yellow solid which separates on standing is collected by filtration and recrystallized from ethyl alcohol to give the product of the example, mp 202°–203° C.

EXAMPLE 3

4-(10H-Pyrido[3,2-b]thieno[3,4-e][1,4]diazepin-6-yl)-1-piperazineethanol, fumarate A mixture of 2.5 g of 6-(methylthio)-10H-pyrido-[3,2-b]thieno[3,4-e][1,4]diazepine (prepared as described in Example 1), 2.6 g of hydroxyethylpiperazine, 15 ml of xylene and 3 drops of glacial acetic acid is stirred at reflux temperature (135°–140° C) overnight. The solvent is evaporated and the resulting thick oil is washed with water. The residue is dissolved in 2N acetic acid and is filtered. The filtrate is made alkaline with ammonium hydroxide resulting in separation of an oil. The mixture is extracted 4 times with methylene chloride. The extracts are dried over magnesium sulfate, then filtered and evaporated to dryness.

The residue is dissolved in 20 ml of ethyl alcohol and a solution of 1.6 g of fumaric acid in 30 ml of ethyl alcohol is added with stirring and cooling. A yellow solid is separated and collected by filtration. The solid is recrystallized from 80 ml of ethyl alcohol to give the product of the example, mp 192°–193° C.

EXAMPLE 4

10-Methyl-6-(4-methyl-1-piperazinyl)-10H-pyrido-[3,2-b]thieno[3,4-e][1,4]diazepine A mixture of 23.1 g of 5,10-dihydro-10-methyl-6H-pyrido[3,2-b]thieno[3,4-e][1,4]diazepin-10-one (prepared according to the general method described in U.S. Pat. No. 3,953,430) and 11.1 g of phosphorus pentasulfide in 250 ml of pyridine is stirred and heated under reflux for 4 hours. The excess pyridine is removed and 300 ml of 5% aqueous sodium carbonate and some methanol is added to the residue followed by overnight stirring. The pH of the resulting mixture is adjusted to 7 with dilute hydrochloric acid. The brown solid is collected and washed with water to give 5,10-dihydro-10-methyl-6H-pyrido[3,2-b]thieno[3,4-e][1,4]diazepin-6-thione.

A 2.3 g portion of sodium metal is dissolved in 400 ml of ethyl alcohol, then 24.7 g of the above compound and 15 ml of methyl iodide is added and the mixture is stirred for about 20 hours. The mixture is cooled and filtered. The brown solid is extracted with ether in a Soxhlet-thimble. The ether is evaporated to give 10-methyl-6-(methylthio)-10H-pyrido[3,4-b]thieno[3,4-e][1,4]diazepine as a yellow solid.

A 2.6 g portion of the above compound, 16 ml of N-methylpiperazine and 3 drops of acetic acid is stirred at reflux temperature (138° C) for 8 hours and then is poured into ice-water. The yellow solid formed is collected and recrystallized from ethyl alcohol to give the product of the example.

We claim:
1. The compound 6-(4-methyl-1-piperazinyl)-10H-pyrido[3,2-b]thieno[3,4-e][1,4]-diazepine.

* * * * *